(12) United States Patent
Pöllmann et al.

(10) Patent No.: US 7,431,885 B2
(45) Date of Patent: Oct. 7, 2008

(54) MEASURING DEVICE FOR THE AMPEROMETRIC MEASUREMENT OF TEST STRIPS

(75) Inventors: Norbert Pöllmann, Eching (DE); Wolfgang Heider, Lenggries (DE); Genrich Siris, München (DE)

(73) Assignee: LRE Medical GmbH, München (DE)

( * ) Notice: Subject to any disclaimer, the term of this patent is extended or adjusted under 35 U.S.C. 154(b) by 0 days.

(21) Appl. No.: 11/752,347

(22) Filed: May 23, 2007

(65) Prior Publication Data

US 2007/0274866 A1 Nov. 29, 2007

(30) Foreign Application Priority Data

May 26, 2006 (DE) .................. 10 2006 024 695

(51) Int. Cl.
*G01N 21/00* (2006.01)
(52) U.S. Cl. .......................... 422/82; 436/95
(58) Field of Classification Search ............... 422/82.02
See application file for complete search history.

(56) References Cited

U.S. PATENT DOCUMENTS 6,964,871 B2 * 11/2005 Bell et al. ................. 436/95

2002/0076349 A1 * 6/2002 Aitken et al. ................. 422/58

FOREIGN PATENT DOCUMENTS

WO WO 2005/102154 * 11/2005

* cited by examiner

*Primary Examiner*—Walter D. Griffin
*Assistant Examiner*—Bobby Ramdhanie
(74) *Attorney, Agent, or Firm*—McCormick, Paulding & Huber LLP

(57) ABSTRACT

A measuring device for the amperometric measurement of test strips 12, each having a test field moistenable by a liquid to be investigated and having measuring electrodes associated with the test field. The device includes at least one test strip receiver 20 for the insertion of a test strip 12, first contact elements arranged in the region of the strip receiver 20 for contacting the measuring electrodes of a test strip 12 located in the strip receiver 20, and an evaluation and control circuit. The strip receiver 20 is formed with a separate unitary housing which on its external side has second external contact elements 50 electrically connected with the first internal contact elements. The external contact elements 50 are designed for contacting opposite contact elements 16 connected with the evaluation and control circuit.

11 Claims, 3 Drawing Sheets

MEASURING DEVICE FOR THE AMPEROMETRIC MEASUREMENT OF TEST STRIPS

CROSS REFERENCE TO RELATED APPLICATION

This application claims priority from German Patent Application No. 10 2006 02469.0 filed May 26, 2006, the entire disclosure of which is incorporated herewith by reference.

BACKGROUND OF THE INVENTION

1. Field of the Invention

The invention concerns a measuring device for the amperometric measurement of test strips each of which has a test field moistenable by a liquid to be investigated and measuring electrodes associated with the test field, which device includes at least one strip receiver for the insertion of a test strip, first contact elements arranged in the region of the test strip receiver for contacting the measuring electrodes of a test strip located in the strip receiver, and a evaluation and control circuit.

2. Prior Art

Known measuring devices of the above-mentioned kind usually have a plastic material housing in which the strip receiver is formed as well as a circuit board receivable in the housing with the evaluation and control circuit. This conception has the disadvantage that it is relatively inflexible, so that the measuring device can be made suitable for different customer desires only at considerable expense. While the adapting of the evaluation and control circuit and the remaining electrical and electronic components to different test strips usually does not involve large problems, for the processing of test strips of a different format or different shape, because of the test strip receiver being formed in the housing, as a rule a new housing has to be designed. This results in high work tool costs for the making of the housings.

The invention has as its basic object the construction of a measuring device of the above-mentioned kind which can be adapted in simple and cost effective ways to test strips of different construction and different format.

SUMMARY OF THE INVENTION

This object is solved in accordance with the invention in that the test strip receiver is formed in a separate unitary housing having on its outer side second external contact elements which are electrically connected with the first internal contact elements and which second external contact elements are designed for making contact with the opposing contact elements of the device which are connected with the evaluation and control circuit.

To match the measuring device to different test strips it is sufficient if the strip receiver as such is changed and put into the device housing. This can be done at a very much lower cost and with much less effort. The unitary separate housing of the strip receiver has, moreover, the advantage that the danger of contamination of the measuring device by the test strips is substantially reduced. The penetration of test fluids into the measuring device can be substantially eliminated.

To simplify the installation of the strip receiver into the measuring device and its connection with the evaluation and control circuit, it is advantageous if the housing of the strip receiver has on its outer side holding elements for holding it to the board carrying the evaluation and control circuit. For example, the housing can be so designed, that it is insertable into a recess of the board and so that it has guide elements on its outer side for guiding the housing on the edges of the board recess.

The making of the housing of the strip receiver can be considerably simplified if the housing has two parts connectable with one another with a separation plane which runs through the strip receiver parallel to the strip support surface. Therefore, parts easily removable from their molds can be made without undercuts, between which parts the first internal contact elements can be laid before the two parts are connected with one another, for example by a snap fit with one another.

The external contact elements are advantageously formed as contact springs which can come into contact with their opposing contact elements formed by conductor paths on the circuit board. The external contact elements can be soldered to their opposing contact elements or they can lie with only mechanical spring tension on their opposing contact elements, which latter case simplifies the exchange of the strip receiver housings, so that one and the same measuring device can easily be reequipped by the user for the processing of different test strips.

The internal contact elements are likewise preferably made as contact springs designed for engagement with the contact pads of the test strips. In this case at least two of the internal contact springs are so formed and arranged that they can succeed in gaining contact with the same contact path of a test strip. With this arrangement in a simple way a switched is formed which turns on the measuring device when the test strip is inserted into the strip receiver and thereby an electric connection between the two contact elements is made.

Preferably, at least one further contact element is also provided which is contactable with one of the contact surfaces of the test strip serving for data communication. The strip receiver is preferably so formed that a test strip located in the strip receiver can be moistened with the liquid to be investigated. In this way one avoids the user coming into contact with a moistened test strip when he inserts it into a strip receiver. To avoid having the user take hold of the test strip upon its removal from the measuring device, in accordance with the invention, a test strip release mechanism is provided in the housing of the strip receiver. This release mechanism preferably includes a release element and an actuating element operable from the outside of the housing, which actuating element upon its actuation causes the release element to lift the first, internal, contact springs which urge the test strip against the strip support surface, so that with an associated appropriate orienting of the measuring device the test strip can fall downwardly out of the test strip receiver, for example into a waste container.

Preferably, the release mechanism and the housing parts of a strip receiver are so designed that the actuating element can be arranged in either of the two housing parts. Therefore, according to the wish of the user the measuring device can be so implemented that the release element is actuatable from the under side of the measuring device or from the upper side of the measuring device. One such release mechanism can, for example, be realized in that a pivotally supported two arm lever is provided which with its one lever arm lies on the first internal contact springs and is held by those springs in that position, with the lever being actuatable by a plunger whose position in the housing parts is so chosen that depending in which housing part it is positioned, it operates on the one lever arm or on the other lever arm.

The invention further concerns a strip receiver of the previously mentioned kind.

BRIEF DESCRIPTION OF THE DRAWINGS

Further features and advantages of the invention will be apparent from the following description which in connection with the accompanying drawings explains the invention by way of an exemplary embodiment. The drawings are.

DESCRIPTION OF THE PREFERRED EMBODIMENTS

Figure 1:
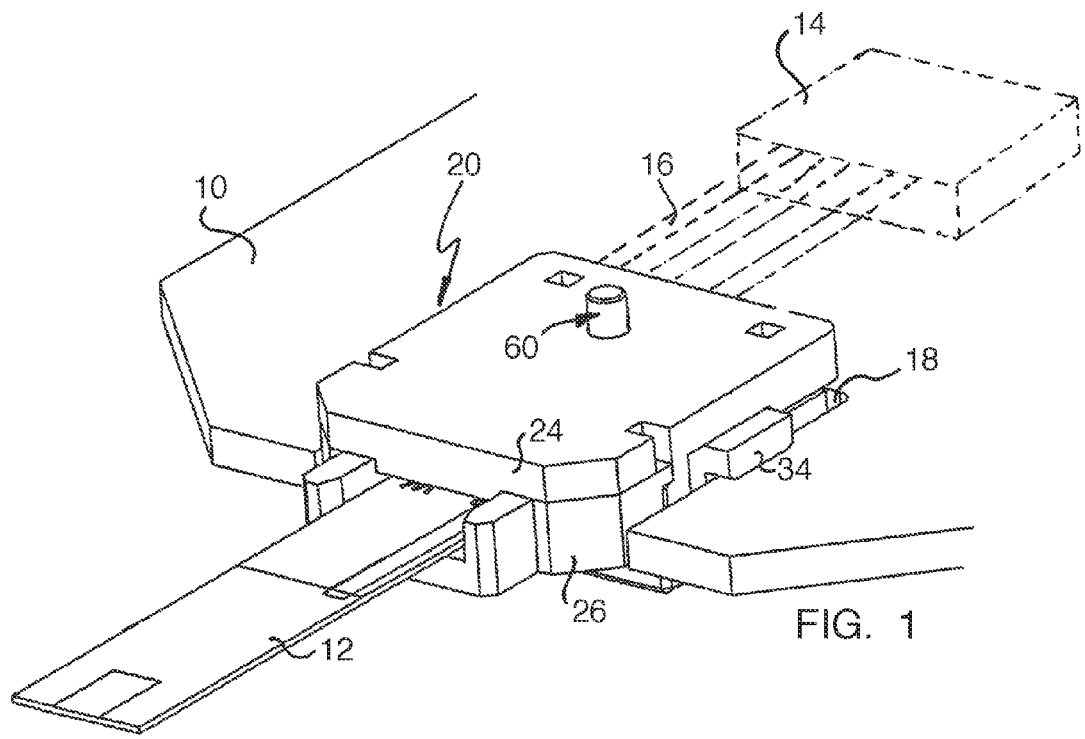
FIG. 1 A partial schematic perspective view of a measuring circuit board with the housing of a strip receiver in which a test strip is located, for a not otherwise illustrated measuring device, FIG. 2 A partial schematic perspective plan view of the opposite side of the housing and circuit board, FIG. 3 A perspective side view of the housing of the strip receiver alone, FIG. 4 A schematic partial view through the housing of FIG. 3 taken in the longitudinal direction, FIG. 5 A partial schematic plan view of the bottom part of the strip receiver housing alone without a test strip, and FIG. 6 A view corresponding to FIG. 5 with an inserted test strip.

In FIG. 1, a circuit board is shown at 10, which circuit board is designed for arrangement in the housing of a measuring device for the amperometric measurement of test strips such as the one shown at 12. Since the measuring device can be made in ways known in themselves, the housing of the measuring device is not illustrated here. The circuit board 10 carries an evaluation and control circuit, which is indicated by a processor 14 and conductor pads 16 shown in broken lines.

At the end facing the viewer, the circuit board 10 has a rectangular recess 18 into which is inserted a strip receiver, indicated generally at 20, for the test strips 12, which receiver will now be described further in more detail.

Figure 3:
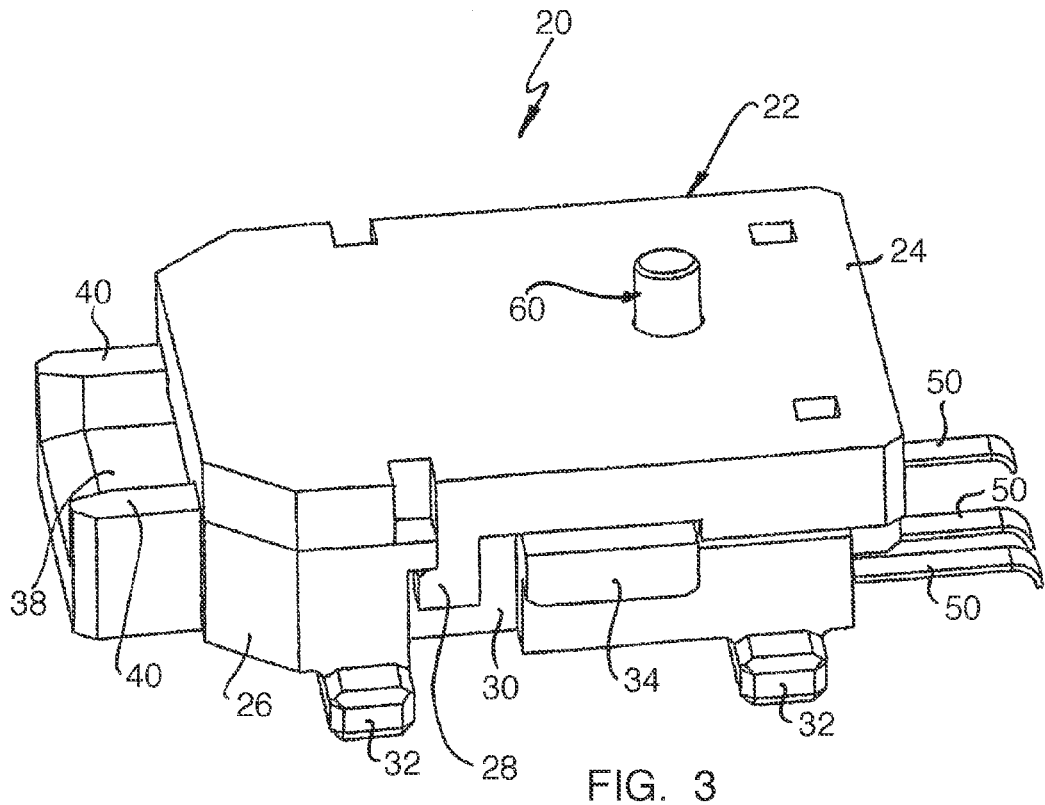

The strip receiver includes a housing 22 with a housing upper part 24 and a housing lower part 26. The two housing parts 24 and 26 are made of plastic material, preferably by way of an injection molding process. On each of the two longitudinal sides of the housing upper part 24 is formed a hook shaped projection 28 which is receivable in a recess 30 formed in the lower housing part when the upper housing part is placed onto the lower housing part 26. By a longitudinal shifting of the housing upper part 24 relative to the housing lower part 26, the two housing parts can be connected with one another as is seen in FIG. 3.

Figure 2:
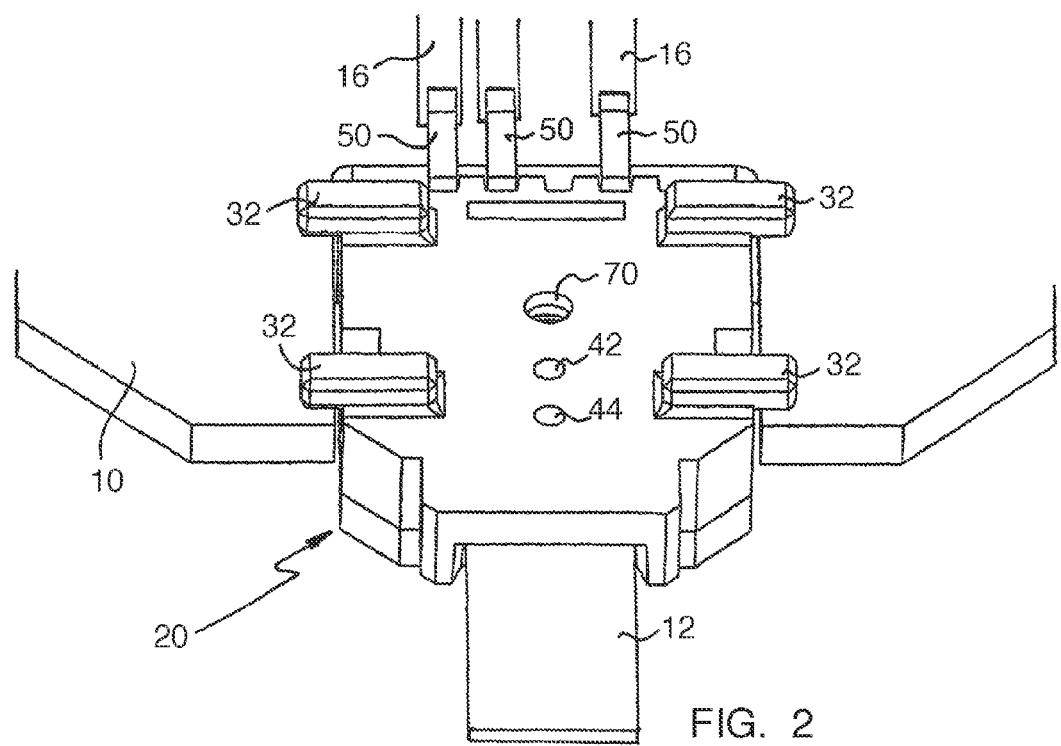

On each of the longitudinal sides of the lower housing part are two laterally projecting lower guide elements 32 and an upper guide element 34. Between which guide elements 32 and 34, the edge portions of the circuit board bordering the recess 18 come to lie when the housing 22 of the strip receiver 20 is pushed into the recess 18, as is seen in FIGS. 1 and 2.

The housing lower part 22 has a strip support surface 38 which is bounded by sidewalls 40 which are spaced from one another by a distance which corresponds to the width of the test strips 12 to be received. In the strip support surface 38 of the housing lower part 26 are two through openings 42, 44 which serve for the application of a liquid to be investigated to the test field of a test strip 12 lying on the strip support surface 38.

Figure 6:
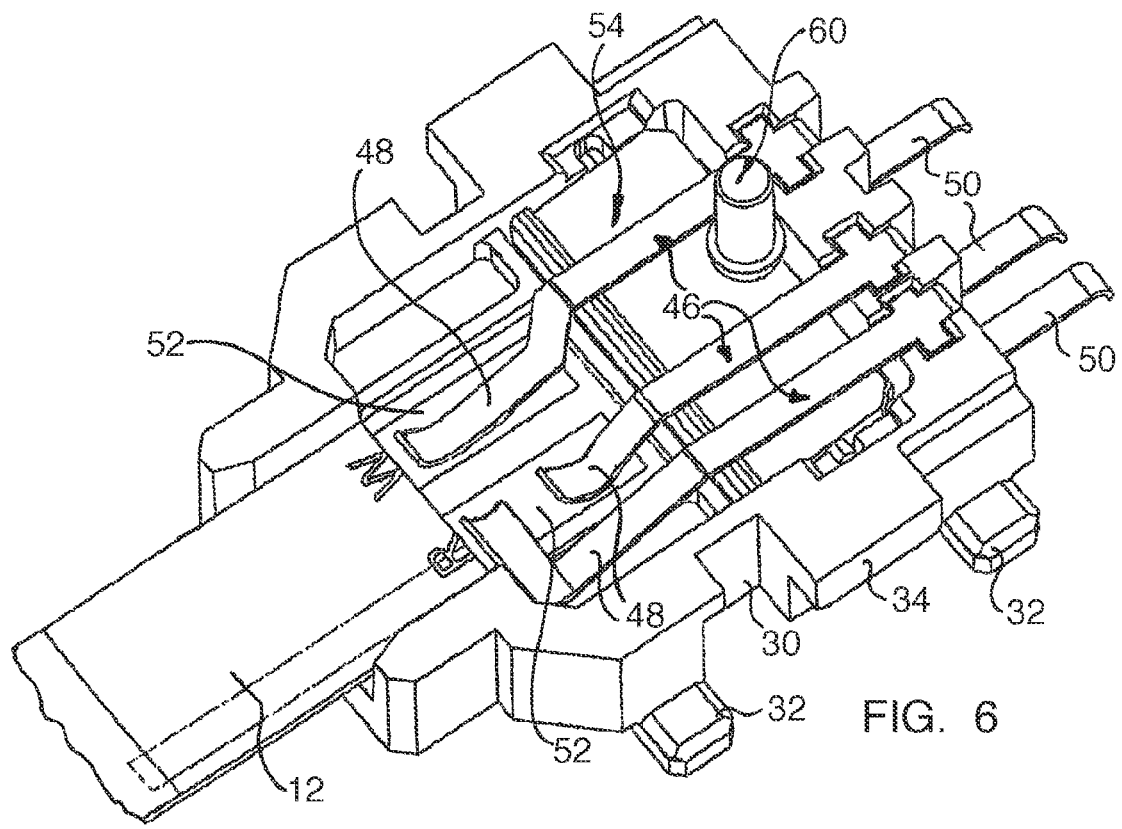

Further, contact springs 46 are fastened to the housing under part 36, each of which has an internal contact section 48 and an external contact section 50. The internal contact section 48 is designed for engagement with one of the two electrode surfaces 52 of the strip 12. The external contact section 50 is designed for engagement with a conductor path 16 of the circuit board 10 as shown in FIG. 2. As can be seen from FIG. 6, two of the contact springs lie with their internal contact sections 48 on the same electrode surface 52 when the test strip 12 lies on the strip support surface 38. These two contact sections 48 therefore are in this way connected with one another or short circuited by the involved electrode surface 52, so that this arrangement of the two contact springs 46 and the electrode surface 52 which electrically connects them can serve as a switch, to, for example, turn on the measuring device upon the insertion of the test strip 12 and to turn off the measuring device upon the removal of the test strip 12.

Figure 4:
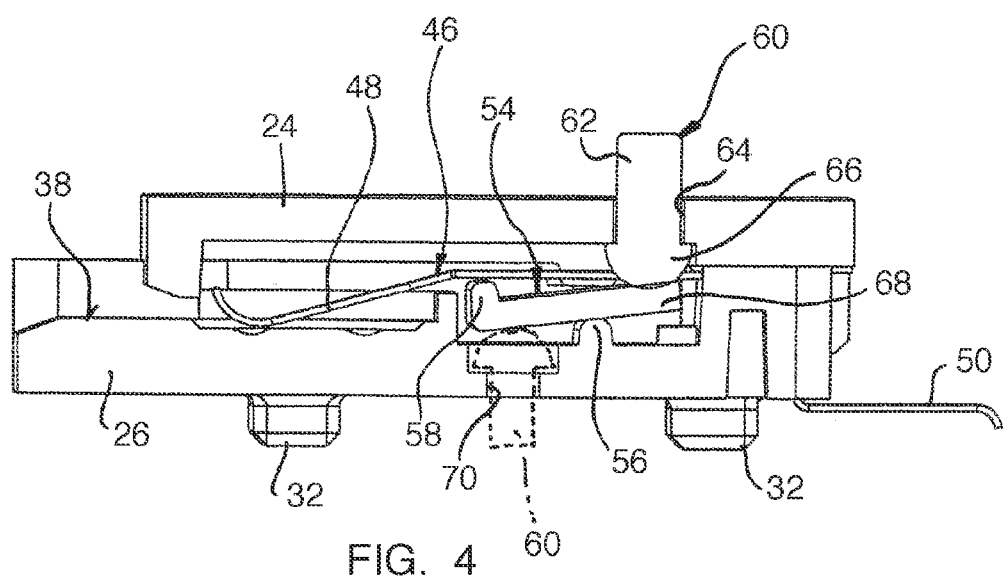
Figure 5:
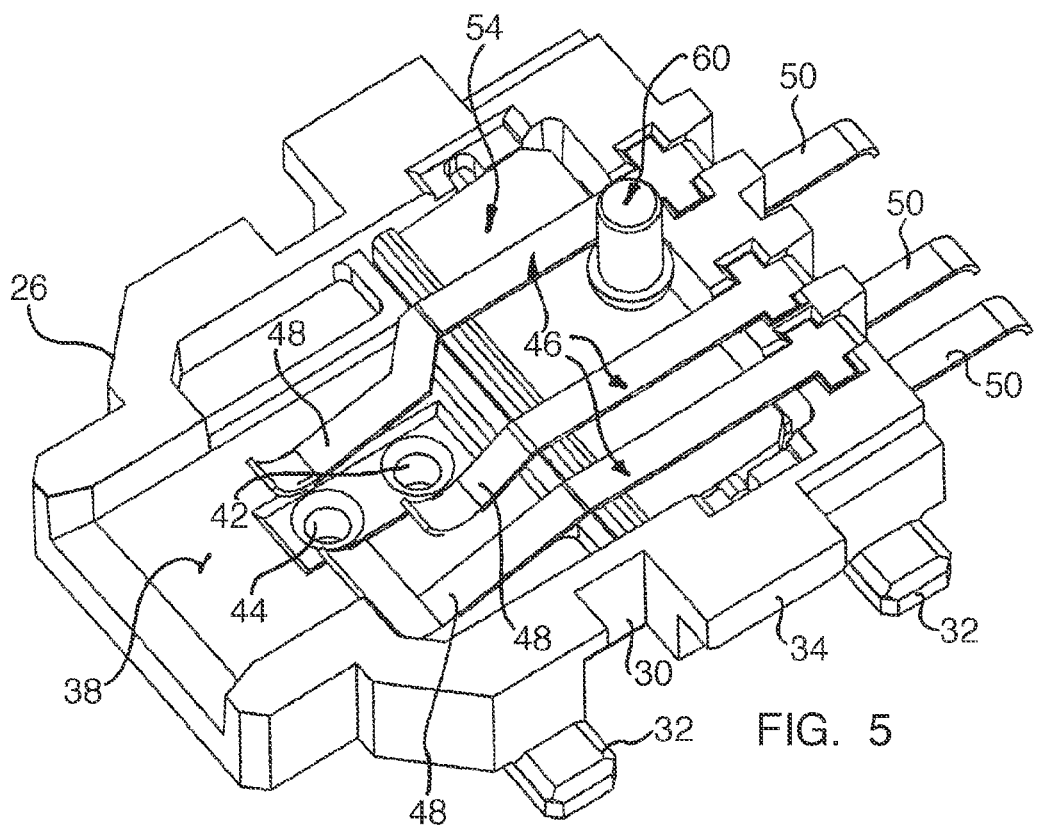

As has already been explained above, the liquid to be tested is first applied through the openings 42 and 44 to the test field of the test strip 12 when the test strip is in the strip receiver. This makes it easier to maintain the pre-established test requirements and at the same time inhibits the user from coming in contact with the liquid to be tested during the insertion of the strip into the strip receiver. To assure that the test strip 12, which has been pushed against the strip support surface 38 by the contact springs 46 in the device, need not be grasped to remove the strip from the measuring device, a release mechanism is provided to lift the contact sections 48 from the electrode surfaces 52. This release mechanism includes a two arm lever 54 which is supported below the internal contact sections 48 on a rib 56 for pivotal movement. The lever 54 lies with a first arm 58 on the under side of the contact sections 48 of the contact springs 46. In the housing upper part 24 of the housing 22 is arranged a plunger 60 which with its shaft part 62 passes through a bore 64 in the housing upper part 24 and which with its plunger head 66 lies on the second lever arm 68. By a depressing of the plunger 60, the lever 54 is pivoted whereby, as seen in FIG. 4, the lever arm 58 moves upwardly and lifts the contact sections 48 from the strip support surface 38 and from the electrode surfaces 52 of the test strip 12. The test strip is now no longer clamped in place and can by an appropriate orienting of the measuring device fall downwardly out of the strip receiver 20.

According to the desire of the customer, the plunger 60 can be arranged for actuation from either the upper side or the lower side of the measuring device. For this purpose, a bore 70 is also provided in the housing bottom portion 26 and into which bore 70 a plunger 60, indicated by broken line, can be placed so that the arrangement is such that the plunger with its plunger head 66 then lies on the under side of the lever arm 58 to lift the lever arm 58 upwardly upon an actuation of the plunger 60.

The external contact sections 50 can also be designed in such a way as to allow them to be soldered to the contact pads 16 of the circuit board 10.

The invention claimed is:

1. A measuring device for the amperometric measurement of test strips each having a test field moistenable by a liquid to be investigated and having measuring electrodes associated with the test field, which device includes at least one strip receiver for the insertion of a test strip, internal contact elements in the region of the strip receiver for contacting measuring electrodes of a test strip located in the strip receiver, and an evaluation and control circuit, characterized in that the strip receiver is formed with a separate unitary housing having on its external side external contacts which are electrically connected with the first internal contact elements, which external contact elements are designed for contacting opposing contact elements which are connected with the evaluation and control circuit, a test strip releasing mechanism being arranged in the housing, the test strip releasing mechanism including a releasing element and an actuating element actuatable from the outside of the housing, which actuating element upon actuation causes the release element to lift up the internal contact elements which clamp the test strip against a strip support surface, the release mechanism and the housing configured such that the actuating element can be made to be actuatable from one or the other of two oppositely arranged sides of the housing, the release mechanism including a pivotally supported two arm lever which lies with one lever arm on the internal contact elements and is held by the internal contact elements in that position, with the lever being actuatable by a plunger whose position in the housing is such that according to which side of the housing receives the plunger, the plunger operates on either the one arm or on the other arm of the lever.

2. The measuring device according to claim 1, further characterized in that the evaluation and control circuit is arranged on a board, and in that the housing on its external side has holding elements for holding the housing to the board.

3. The measuring device according to claim 2, further characterized in that the housing is insertable into a recess of the board and on its external side has guide elements for guiding the housing on the edges of the recess.

4. The measuring device according to claim 1, further characterized in that the housing includes two parts connectable with one another and which parts when so connected with one another have a separation plane which runs through the strip receiver parallel to a strip support surface.

5. The measuring device according to claim 4, further characterized in that the housing parts are connectable with one another with a snap fit.

6. The measuring device according to claim 4, further characterized in that the housing parts are made of a plastic material.

7. The measuring device according to claim 2, further characterized in that the external contact elements are each made from a contact spring and in that the opposing contact element associated with that contact spring is formed by a conductor path on the board, with the contact spring being designed to engage its associated opposing contact element under spring pressure.

8. The measuring device according to claim 2, further characterized in that the external contact elements are connectable by way of solder to their associated opposing contact elements.

9. The measuring device according to claim 1, further characterized in that the internal contact elements are formed as contact springs designed for engagement with the contact pads of the test strips.

10. The measuring device according to claim 9, further characterized in that at least two of the internal contact springs are so formed and arranged that they are able to make contact with the same contact path of a test strip.

11. The measuring device according to claim 1, further characterized in that at least one further contact element is provided which is contactable with a data communication serving contact surface of the test strip.

* * * * *